United States Patent
Donegan et al.

(10) Patent No.: US 9,604,895 B2
(45) Date of Patent: Mar. 28, 2017

(54) LACTATE PRODUCTION PROCESS

(71) Applicant: PLAXICA LIMITED, Redcar (GB)

(72) Inventors: Stephen Donegan, London (GB);
Philip James Goodier, London (GB);
Edward Leslie Marshall, London
(GB); **Urvish Rameshchandra
Pandya, London (GB); Ajitkumar
Mukundrai Patel**, London (GB)

(73) Assignee: Plaxica Limited, Redcar (GB)

( * ) Notice: Subject to any disclaimer, the term of this patent is extended or adjusted under 35 U.S.C. 154(b) by 0 days.

(21) Appl. No.: 14/912,372

(22) PCT Filed: Sep. 5, 2014

(86) PCT No.: PCT/GB2014/052700
§ 371 (c)(1),
(2) Date: Feb. 16, 2016

(87) PCT Pub. No.: WO2015/033159
PCT Pub. Date: Mar. 12, 2015

(65) Prior Publication Data
US 2016/0185704 A1  Jun. 30, 2016

(30) Foreign Application Priority Data
Sep. 6, 2013 (GB) .................................. 1315929.8

(51) Int. Cl.
| | |
|---|---|
| *C07C 59/08* | (2006.01) |
| *C07C 51/02* | (2006.01) |
| *C01B 7/03* | (2006.01) |
| *C07C 67/08* | (2006.01) |
| *C07C 51/295* | (2006.01) |
| *C07C 51/41* | (2006.01) |
| *C01D 1/04* | (2006.01) |
| *C01D 3/04* | (2006.01) |
| *A61K 35/744* | (2015.01) |
| *A01N 63/02* | (2006.01) |

(52) U.S. Cl.
CPC ................ *C07C 51/02* (2013.01); *C01B 7/03* (2013.01); *C01D 1/04* (2013.01); *C01D 3/04* (2013.01); *C07C 51/295* (2013.01); *C07C 51/41* (2013.01); *C07C 59/08* (2013.01); *C07C 67/08* (2013.01); *A01N 63/02* (2013.01); *A61K 35/744* (2013.01)

(58) Field of Classification Search
CPC ...... A61K 35/744; A01N 63/02; C07C 59/08; C07C 51/02
See application file for complete search history.

(56) References Cited

U.S. PATENT DOCUMENTS

| | | | |
|---|---|---|---|
| 2,024,565 A | 12/1935 | Braun | |
| 3,547,810 A | 12/1970 | Cooper | |
| 4,339,547 A | 7/1982 | Corbett et al. | |
| 4,444,881 A | 4/1984 | Urbas | |
| 5,510,526 A | 4/1996 | Baniel et al. | |
| 2004/0033573 A1* | 2/2004 | Norddahl ............... | C12P 7/56 435/139 |
| 2005/0119448 A1 | 6/2005 | Matsuda et al. | |

FOREIGN PATENT DOCUMENTS

| | | |
|---|---|---|
| EP | 2 669 305 A1 | 12/2013 |
| GB | 400413 A | 10/1933 |
| GB | 579970 A | 8/1946 |
| WO | 2012/052703 A1 | 4/2012 |
| WO | 2012/065002 A1 | 5/2012 |
| WO | 2012/131299 A1 | 10/2012 |
| WO | 2013/140188 A1 | 9/2013 |

OTHER PUBLICATIONS

International Search Report corresponding to PCT/GB2014/052700 mailed Dec. 11, 2014; 4 pages.
Raharja, S. et al., "Design of a Continuous Process for the Alkaline Treatment of Xylose into Lactic Acide," *The Canadian Journal of Chemical Engineering* (Oct. 1, 1997) 75:913-920.
Freudenberg, Karl et al., "Die Konfiguration der Mandelsaure and anderer [alpha]-Oxy-säuren," *Berichte Der Deutschen Chemischen Gesellschaft* (Jan. 10, 1923); pp. 193-200.

* cited by examiner

*Primary Examiner* — Gregory Listvoyb
(74) *Attorney, Agent, or Firm* — Kilpatrick Townsend & Stockton LLP (57) ABSTRACT

A process for producing lactic acid is provided. The process comprises (a) reacting a stream rich in saccharide with sodium hydroxide in the presence of water to produce a reaction mixture comprising sodium lactate; (b) reacting at least a portion of the sodium lactate with HCl to produce lactic acid and sodium chloride; (c) converting at least a portion of the sodium chloride to chlorine and sodium hydroxide; and (d) recycling at least a portion of the sodium hydroxide produced in step (c) to step (a). Also provided are processes for the production of alkyl lactate, oligomeric lactic acid, lactide, alkyl lactyllactate, poly-lactic acid, propylene glycol and acrylic acid.

20 Claims, 2 Drawing Sheets

LACTATE PRODUCTION PROCESS

FIELD OF THE INVENTION

The present invention relates to processes for the production of lactic acid and $C_{1-6}$ alkyl lactate from saccharide. The invention also relates to processes for producing related products such as oligomeric lactic acid, lactide, alkyl lactyllactate and/or poly-lactic acid.

BACKGROUND OF THE INVENTION

Lactic acid is an important industrial chemical, which finds use as a feedstock in the biopolymer industry. Today, virtually all large scale production of the lactic acid available commercially is manufactured by fermentation processes, see for example Strategic Analysis of the Worldwide Market for Biorenewable Chemicals M2F2-39, Frost and Sullivan, 2009. In a typical fermentation process, biomass is fermented with microorganisms to produce either D- or L-lactic acid, most commonly L-lactic acid. Companies such as Cargill and Purac (now Corbion) operate large-scale fermentation processes for the production of optically active lactic acid. Many patent publications relate to recovery of lactic acid from fermentation mixtures, which can be challenging, and a number of patent documents rely on the preparation of a complex between lactic acid and an amine for the recovery (see, for example, U.S. Pat. Nos. 4,444,881, 5,510,526).

Chemical processes for preparing lactic acid from carbohydrates are known. For example, GB 400,413, dating from 1933, describes an improved process for preparing lactic acid or lactates comprising reacting a carbohydrate-containing material with a strong alkali at a temperature of at least 200° C., preferably at a pressure of at least 20 atmospheres, and recovering the lactic acid so produced by adding sulfuric acid or zinc sulfate to the reaction mixture. Hydrocyanation of acetaldehyde has also been used as a synthetic route for accessing lactic acid.

WO 2012/052703 describes an improved process for the production of a complex of lactic acid and either ammonia or an amine, which does not involve production of lactic acid by fermentation. The process comprises reacting one or more saccharides with barium hydroxide to produce a first reaction mixture comprising barium lactate, and contacting at least part of the first reaction mixture with ammonia or an amine and with carbon dioxide, or with the carbonate and/or bicarbonate salt of ammonia or an amine, to produce a second reaction mixture comprising the complex and barium carbonate. This process, which involves preparation of barium salts, has significant advantages over prior art processes. It does, however, have some disadvantages: specifically, if it is required to recycle the barium, a barium carbonate calcination step is required. Calcination (also referred to as calcining) is a thermal treatment process in absence of air applied to ores and other solid materials to bring about a thermal decomposition, phase transition, or removal of a volatile fraction. The process of calcination derives its name from its most common application, the decomposition of calcium carbonate (limestone) to calcium oxide (lime) and carbon dioxide. The terms calcination, and calcine (the product of calcination), are typically used regardless of the actual minerals undergoing thermal treatment. Whilst barium carbonate calcination is feasible, the technology is not currently widely operated at industrial scale.

In addition, carrying out the process described in WO2012/052703 on an industrial scale requires facilities adapted to handle and transport large quantities of barium salts. Processing solutions for large scale use of barium salts exist. However, there remains a need for improved processes for generating lactic acid and related materials, which still provide acceptable yields of complex but which avoid the disadvantages associated with use of barium salts.

SUMMARY OF THE INVENTION

In a first aspect, the present invention provides a process for the production of lactic acid comprising:
(a) reacting a stream rich in saccharide with sodium hydroxide in the presence of water to produce a reaction mixture comprising sodium lactate;
(b) reacting at least a portion of the sodium lactate with HCl to produce lactic acid and sodium chloride;
(c) converting at least a portion of the sodium chloride to chlorine and sodium hydroxide; and
(d) recycling at least a portion of the sodium hydroxide produced in step (c) to step (a).

DETAILED DESCRIPTION OF THE INVENTION

In the first aspect of the process of the invention, a stream rich in saccharide is reacted with sodium hydroxide. The saccharide present in said stream may be a mono-, di-, tri-, oligo- or poly-saccharide, with disaccharides and, especially, monosaccharides, being preferred. Preferably, the stream rich in saccharide is a stream rich in monosaccharide. In some preferred embodiments, at least 50 wt % of the saccharides, at least 60 wt % of the saccharides, at least 70 wt % of the saccharides, at least 80 wt % of the saccharides, at least 90 wt % of the saccharides, at least 95 wt % of the saccharides present in said stream rich in saccharides are monosaccharides. Suitable monosaccharides include for example hexose monosaccharides, for example glucose, fructose, psicose, galactose and mannose, and pentose monosaccharides, for example arabinose, xylose, ribose, xylulose and ribulose. In one embodiment, the stream rich in saccharide comprises glucose. In another embodiment, the stream rich in saccharide comprises fructose. In another embodiment, the stream rich in saccharide comprises mannose. In another embodiment, the stream rich in saccharide comprises xylose. Mixtures of saccharides may be present in the stream rich in saccharides. For example, a mixture of two or more monosaccharides, for example a mixture of glucose and fructose, may be present. Monosaccharides may be obtained from any known monosaccharide source, for example a higher saccharide such as sucrose, starch or cellulose. In some embodiments, the stream rich in saccharide may contain a mixture of glucose and fructose (known as invert sugar) obtained from sucrose, for example by enzymatic hydrolysis using a sucrase or invertase, or by heating the disaccharide in the presence of an acidic catalyst such as sulphuric acid, citric acid or ascorbic acid. In some embodiments, the stream rich in saccharide may contain glucose obtained by enzymatic hydrolysis (e.g. using an amylase) of starch contained in biomass feedstocks, for example maize, rice or potatoes. In some embodiments, the stream rich in saccharide may contain glucose obtained by hydrolysis of cellulose (e.g. enzymatic hydrolysis using one or more cellulases) contained in biomass feedstocks. The stream rich in saccharides may contain components other than saccharides, for example it may include other components of biomass such as lignin or lignin-derived products. Spent chemicals from processing of biomass may, for example, also be present. Water will typically be present. In some embodiments, at least 50 wt %, at least 60 wt %, at least 70 wt %, at least 80 wt %, at least 90 wt %, at least 95 wt % of the material other than water present in the stream rich in saccharide is saccharide (e.g. monosaccharide).

The reaction between saccharide and sodium hydroxide is carried out in the presence of water. As discussed above, some sources of saccharide contain water, and such feedstocks may readily be used in the process of the invention. In certain embodiments, the reaction between the saccharide and sodium hydroxide may take place in the presence of additional water (i.e. additional to that present in the starting materials). The reaction between the saccharide and sodium hydroxide may also, if desired, take place in the presence of one or more organic solvents, for example an oxygenate such as an alcohol, ester, ether, or ketone; and/or in the presence of one or more reactive extractants such as an amine. However, in a preferred embodiment, the reaction between the saccharide and sodium hydroxide does not take place in the presence of an organic solvent, i.e. water is the only solvent. In some embodiments the weight ratio of the total amount of water used in step (a) to saccharide is in the range of from 0.5:1 to 9:1, more preferably in the range of from 1.25 to 4:1, still more preferably in the range of from 1.5:1 to 4:1, most preferably in the range of from 3:1 to 4:1.

Sodium hydroxide reacts with saccharide to produce sodium lactate. Any form of sodium hydroxide may be used in the process of the invention. Sources of sodium hydroxide such as sodium oxide may be used in the process of the invention, sodium oxide being converted into sodium hydroxide in the presence of water. The sodium hydroxide generated in situ reacts with saccharide to produce sodium lactate. The ratio of sodium hydroxide to saccharide should be sufficient to effect good conversion of saccharide to sodium lactate. Preferably, the molar ratio of sodium hydroxide to saccharide (calculated as monosaccharide) is at least 2:1. Excess quantities of sodium hydroxide may be used, for example the molar ratio of sodium hydroxide to saccharide (calculated as monosaccharide) may be up to 10:1. In some preferred embodiments, the molar ratio of sodium hydroxide to saccharide (calculated as monosaccharide) is in the range of from 2:1 to 6:1, more preferably 2:1 to 4:1, still more preferably 2:1 to 3:1. The present invention also encompasses molar ratios of sodium hydroxide to saccharide (calculated as monosaccharide) that are lower than 2:1; however use of sub-stoichiometric quantities of sodium hydroxide will generally lead to lower conversion of saccharide to sodium lactate. Thus in some embodiments, the molar ratio of sodium hydroxide to saccharide (calculated as monosaccharide) is at least 1.5:1, for example in the range of from 1.5:1 to 6:1, more preferably in the range of from 1.6:1 to 4:1; still more preferably in the range of from 1.8:1 to 2.5:1, yet more preferably in the range of 1.9:1 to 2.1:1.

Conversion of saccharide to sodium lactate may be carried out at ambient temperature, although the reaction is preferably carried out at elevated temperature, for example at a temperature of up to 160° C., preferably up to 110° C. Preferably, saccharide is reacted with sodium hydroxide at a temperature in the range of from 10 to 160° C., more preferably at a temperature in the range of from 60 to 110° C. In some embodiments, saccharide is reacted with sodium hydroxide in water at reflux.

In a preferred embodiment, saccharide (e.g. monosaccharide) in water and sodium hydroxide in water are admixed over a period of time at elevated temperature. For example, a mixture of saccharide (e.g. monosaccharide) and water may be added over a period of time to a mixture of sodium hydroxide and water that is at elevated temperature, for example at a temperature of from 60 to 110° C. Slow addition of saccharide (e.g. monosaccharide) generally leads to a reduction in the formation of side products during the process of the invention, and leads to an improved conversion of saccharide (e.g. monosaccharide) into sodium lactate. Preferably the saccharide (e.g. monosaccharide) in water is added over a period of at least 10 minutes, more preferably at least 30 minutes, still more preferably over at least 1 hour. Preferably the concentration of saccharide in water is at least 0.2 M. In some preferred embodiments the concentration of saccharide in water is in the range of from 0.2 to 4.0 M, more preferably in the range of from 0.5 to 4.0 M. The reaction of saccharide with sodium hydroxide produces a reaction mixture comprising sodium lactate. The process typically leads to the production of racemic sodium lactate.

If desired, the reaction mixture may be concentrated following step (a) by removal of water (e.g. prior to step (b)), for example by distillation, evaporation or membrane separation, and the resulting portion of the reaction mixture used in step (b).

In step (b), at least a portion of the sodium lactate is reacted with HCl to produce lactic acid and sodium chloride. Normally, most or all of the sodium lactate from step (a) is reacted with HCl (e.g. all of the sodium lactate other than, for example, samples removed for analysis/quality control procedures).

The HCl may be provided in any suitable form, for example as HCl gas or as a solution in a suitable solvent. Preferably the HCl is aqueous hydrochloric acid, more preferably concentrated aqueous hydrochloric acid (i.e. about 37% aqueous hydrochloric acid). In step (b) some water will usually be present, for example the sodium lactate is typically provided as a solution/suspension in water, even in the case where some water is removed following step (a), as discussed above. The HCl used may be aqueous hydrochloric acid (e.g. concentrated aqueous hydrochloric acid), and so may be a source of water also. Step (b) is carried out at a temperature suitable to effect conversion of sodium lactate to lactic acid and sodium chloride, for example at a temperature in the range of from 5 to 125° C. In one embodiment step (b) is carried out at ambient temperature. In one embodiment step (b) is carried out under reflux.

Preferably the amount of HCl used should be sufficient to react with the sodium lactate, as well as to neutralise other sodium species present in the reaction mixture resulting from step (a), such as unreacted sodium hydroxide or other organic sodium salts. In a preferred embodiment, the molar ratio of sodium hydroxide used in step (a) to HCl used in step (b) is in the range of from 1:1 to 1:5, more preferably in the range of from 1.0:1.0 to 1.0:1.5, still more preferably in the range of from 1.0:1.0 to 1.0:1.2. In another embodiment, the molar ratio of sodium lactate to HCl is in the range of from 1:1 to 1:5. The present invention also encompasses molar ratios of sodium lactate to HCl that are lower than 1:1; however use of sub-stoichiometric quantities of HCl will generally lead to lower conversion of sodium lactate to lactic acid. For example, the molar ratio of sodium lactate to HCl may be in the range of from 1:0.9 to 1:5. Where downstream processing of the lactic acid requires an acidic environment, for example where lactic acid is reacted with a $C_{1-6}$ alkyl alcohol under acidic conditions to produce the corresponding alkyl lactate, it may be preferred to use a molar excess of HCl in step (b) compared with the amount of NaOH used in step (a). Thus in some preferred embodiments, the molar ratio of the amount of HCl used in step (b) compared to the amount of sodium hydroxide used in step (a) is in the range of from 1.01:1.00 to 1.50:1.00, preferably from 1.01:1.00 to 1.20:1.00, more preferably from 1.01:1.00 to 1.10:1.00.

In a preferred embodiment, step (b) comprises admixing at least a portion of the reaction mixture from step (a) with HCl and with a $C_{3-6}$ alkyl alcohol. Those alkyl alcohols are preferred solvents since, in the presence of sodium chloride, lactic acid and water, a biphasic mixture is produced. Lactic acid preferentially partitions into the alkyl alcohol phase and sodium chloride preferentially partitions into the aqueous phase. The partitioning may be promoted by the use of suitable phase transfer catalysts. Thus, the use of a $C_{3-6}$ alkyl alcohol enables separation of sodium chloride from lactic acid by liquid-liquid phase separation. n-Butanol and i-propanol are preferred solvents, with n-butanol being most preferred, since it facilitates separation of sodium chloride and lactic acid with particularly good yields of both products. Such processes, which require handling of liquids only, rather than liquids and solids, are particularly suited for industrial scale operation. In addition, where downstream processing of the products involves removal of water, for example where lactic acid is reacted with alkyl alcohol to produce alkyl lactate, processes of this type are also advantageous since they reduce the need for energy intensive distillation/evaporation processes. Separation of sodium chloride from lactic acid by liquid-liquid phase separation also provides the sodium chloride in a convenient form for transportation to and use in step (c).

Accordingly, in a preferred embodiment, the process of the invention comprises (a) reacting a stream rich in saccharide with sodium hydroxide in the presence of water to produce a reaction mixture comprising sodium lactate; (b) admixing at least a portion of the reaction mixture from step (a) with HCl and with a $C_{3-6}$ alkyl alcohol to produce a biphasic mixture comprising lactic acid and sodium chloride; (b') separating sodium chloride and water from lactic acid by liquid-liquid phase separation; (c) converting at least a portion of the sodium chloride to chlorine and sodium hydroxide; and (d) recycling at least a portion of the sodium hydroxide produced in step (c) to step (a). In one embodiment the $C_{3-6}$ alkyl alcohol is admixed with sodium lactate prior to admixing with HCl. In another embodiment HCl is admixed with sodium lactate prior to admixing with the $C_{3-6}$ alkyl alcohol. In another embodiment a mixture comprising the $C_{3-6}$ alkyl alcohol and HCl is admixed with sodium lactate. In a preferred embodiment the weight ratio of the total amount of water used in step (a) to saccharide is in the range of from 1.25:1 to 4:1, for example from 3:1 to 4:1. In a preferred embodiment the molar ratio of sodium hydroxide to saccharide (calculated as monosaccharide) used in step (a) is in the range of from 2:1 to 4:1, and the molar ratio of HCl used in step (b) to sodium hydroxide used in step (a) is in the range of from 1.01:1.00 to 1.20:1.00. In a preferred embodiment the molar ratio of sodium hydroxide to saccharide (calculated as monosaccharide) used in step (a) is in the range of from 1.8:1 to 2.5:1, and the molar ratio of HCl used in step (b) to sodium hydroxide used in step (a) is in the range of from 1.01:1.00 to 1.20:1.00, for example from 1.01:1.00 to 1.10:1.00. In some preferred embodiments the volume ratio of $C_{3-6}$ alkyl alcohol to water in step (b) is in the range of from 1:1 to 5:1, for example from 2:1 to 5:1. In some preferred embodiments the $C_{3-6}$ alkyl alcohol used in step (b) is n-butanol and the volume ratio of n-butanol to water in step (b) is in the range of from 1:1 to 5:1, for example from 2:1 to 5:1. In some preferred embodiments the weight ratio of the total amount of water to saccharide used in step (a) is in the range of from 1.25:1 to 4:1, for example from 3:1 to 4:1, the molar ratio of sodium hydroxide to saccharide (calculated as monosaccharide) used in step (a) is in the range of from 2:1 to 4:1, the molar ratio of HCl used in step (b) to sodium hydroxide used in step (a) is in the range of from 1.01:1.00 to 1.20:1.00, and the volume ratio of $C_{3-6}$ alkyl alcohol to water in step (b) is in the range of from 2:1 to 5:1. In some preferred embodiments the weight ratio of water to saccharide used in step (a) is in the range of from 1.25:1 to 4:1, for example from 3:1 to 4:1, the molar ratio of sodium hydroxide to saccharide (calculated as monosaccharide) used in step (a) is in the range of from 1.8:1 to 2.5:1, the molar ratio of HCl used in step (b) to sodium hydroxide used in step (a) is in the range of from 1.01:1.00 to 1.20:1.00, for example from 1.01:1.00 to 1.10: 1.00, the $C_{3-6}$ alkyl alcohol used in step (b) is n-butanol, and the volume ratio of n-butanol to water used in step (b) is in the range of from 1:1 to 5:1, for example from 2:1 to 5:1.

Preferably, following acidification, the volume of the reaction mixture obtained following step (b) is reduced by removal of water (for example by distillation, evaporation or membrane separation), prior to carrying out further processing of the mixture (for example converting the lactic acid into alkyl lactate). Carrying out acidification prior to concentration rather than after concentration is preferred since the presence of additional solvent during step (b) allows for improved dissipation of heat generated during the exothermic acidification step. In some embodiments, the volume of the mixture obtained following step (b) is reduced by at least 10%, at least 20%, at least 30%, at least 40% or at least 50%, prior to admixing with $C_{1-6}$ alkyl alcohol.

As discussed above, the lactic acid obtained by the process may be converted into a $C_{1-6}$ alkyl lactate, e.g. n-butyl lactate. Conversion into a $C_{1-6}$ alkyl lactate may offer advantages in respect of recovery and/or purification of lactate/lactic acid-containing species, alkyl lactates being less corrosive and less susceptible to oligomerisation than lactic acid, and so easier to handle and manipulate. Accordingly, the invention provides a process for the production of a $C_{1-6}$ alkyl lactate comprising: producing lactic acid according to the invention, and reacting at least a portion of the lactic acid with a $C_{1-6}$ alkyl alcohol to produce the corresponding alkyl lactate.

Where lactic acid is reacted with a $C_{1-6}$ alkyl alcohol to produce the corresponding alkyl lactate, the $C_{1-6}$ alkyl alcohol is preferably ethanol, n-propanol, i-propanol or n-butanol, most preferably n-butanol. The use of a $C_{1-6}$ alkyl alcohol such as n-butanol results in an alkyl lactate having a boiling point which facilitates separation from other components present in the reaction mixture by distillation but which does not require excessive energy input for its recovery.

The reaction between lactic acid and $C_{1-6}$ alkyl alcohol is typically catalysed by the presence of acid, preferably HCl (e.g. excess HCl introduced during step (b)).

The reaction between lactic acid and $C_{1-6}$ alkyl alcohol is suitably carried out at a temperature in the range of from 50 to 150° C., preferably 50 to 125° C., for example 65 to 120° C., especially 95 to 115° C. In some preferred embodiments the reaction is carried out under reflux, with removal of water. The $C_{1-6}$ alkyl alcohol may be used as solvent as well as reactant. An additional organic solvent may be present if desired.

In order for good yields of $C_{1-6}$ alkyl lactate to be obtained, it is necessary to remove water from the reaction mixture, for example by evaporation or distillation, e.g. distillation under reduced pressure. Water formed from the reaction of lactic acid and $C_{1-6}$ alkyl alcohol is typically removed as it is formed during the esterification process. If present any additional water remaining from an earlier step in the process will also typically be removed during the esterification process. For example, a mixture comprising water, n-butanol, lactic acid, HCl and optionally sodium chloride may be heated under reflux with water being removed.

However, if desired, water other than that formed during the esterification reaction may be removed prior to esterification. Where a $C_{3-6}$ alkyl alcohol is used, for example n-butanol, water and sodium chloride may be removed by liquid-liquid phase separation of a biphasic mixture, with lactic acid preferentially partitioning into the alkyl alcohol phase and sodium chloride preferentially partitioning into the aqueous phase. As described above, processes of this type are particularly advantageous since they reduce the need for energy intensive distillation/evaporation processes.

Accordingly, in a preferred embodiment, the process of the invention comprises: (a) reacting a stream rich in saccharide with sodium hydroxide in the presence of water to produce a reaction mixture comprising sodium lactate; (b) admixing at least a portion of the reaction mixture from step (a) with HCl and with a $C_{3-6}$ alkyl alcohol to produce a biphasic mixture comprising lactic acid and sodium chloride; (b') separating sodium chloride and water from lactic acid by liquid-liquid phase separation; (b") reacting at least a portion of the lactic acid with $C_{3-6}$ alkyl alcohol to produce the corresponding alkyl lactate; (c) converting at least a portion of the sodium chloride to chlorine and sodium hydroxide; and (d) recycling at least a portion of the sodium hydroxide produced in step (c) to step (a).

Alternatively, in a particularly preferred embodiment, the volume of the reaction mixture obtained following step (b) is reduced by removal of water (e.g. by distillation, evaporation or membrane separation), prior to reacting the lactic acid with a $C_{1-6}$ alkyl alcohol (i.e. step (b) is carried out in the absence of $C_{1-6}$ alkyl alcohol, the volume of the aqueous mixture is then reduced, and the resulting concentrate admixed with $C_{1-6}$ alkyl alcohol). In some embodiments, the volume of the mixture obtained following step (b) is reduced by at least 10%, at least 20%, at least 30%, at least 40% or at least 50%, prior to admixing with $C_{1-6}$ alkyl alcohol. As discussed above, during esterification it is necessary to remove water from the reaction mixture, for example by evaporation or distillation. Typically, under the esterification reaction conditions a mixture of water and alkyl alcohol is evaporated. It has been found that the amount of $C_{1-6}$ alkyl alcohol and the energy input required in the esterification step in order to produce good yields of $C_{1-6}$ alkyl lactate is significantly reduced if the volume of the acidified aqueous mixture obtained following step (b) is reduced beforehand by removing water. In some embodiments, the volume of the mixture obtained following step (b) is reduced by an amount in the range of from 10% to 80%, from 10% to 60%, from 10% to 40%, from 10% to 20%, from 20% to 80%, from 20% to 60%, from 20% to 40%, from 30% to 80%, from 30% to 60%, from 30% to 40%, from 40% to 80%, from 40% to 60%, from 50% to 80%, or from 50% to 60%, prior to admixing with $C_{1-6}$ alkyl alcohol. Mixtures which are only partially concentrated typically have improved properties in terms of ease of handling and reduced occurrence of blockages when used in large scale industrial process plants, compared with more concentrated mixtures.

As an alternative to separating sodium chloride and water from lactic acid by liquid-liquid phase separation, where lactic acid is reacted with $C_{1-6}$ alkyl alcohol to produce the corresponding alkyl lactate, sodium chloride may be separated from $C_{1-6}$ alkyl lactate following the reaction of lactic acid with the $C_{1-6}$ alkyl alcohol, for example in the case where liquid-liquid phase separation has not been carried out at an earlier stage. The product mixture from step (b") does not normally contain significant amounts of water, since water will normally have been removed as part of the esterification process. As a result, sodium chloride typically has poor solubility in the product mixture and so it may be separated from $C_{1-6}$ alkyl lactate by, for example, filtration of the product mixture obtained following esterification, or by decanting or siphoning off the liquid phase. Accordingly, in one embodiment the process of the invention comprises: (a) reacting a stream rich in saccharide with sodium hydroxide in the presence of water to produce a reaction mixture comprising sodium lactate; (b) admixing at least a portion of the reaction mixture from step (a) with HCl and with a $C_{1-6}$ alkyl alcohol to produce lactic acid and sodium chloride; (b") reacting at least a portion of the lactic acid with the $C_{1-6}$ alkyl alcohol to produce the corresponding alkyl lactate; (b"') separating solid sodium chloride from the $C_{1-6}$ alkyl lactate (e.g. by filtration); (c) converting at least a portion of the sodium chloride to chlorine and sodium hydroxide; and (d) recycling at least a portion of the sodium hydroxide produced in step (c) to step (a). Where a $C_{3-6}$ alkyl alcohol is used (e.g. n-butanol), sodium chloride may be separated from $C_{3-6}$ alkyl lactate by liquid-liquid phase separation. In that embodiment, following reaction of lactic acid with $C_{3-6}$ alkyl alcohol, the product mixture is admixed with water to obtain a biphasic mixture comprising water, $C_{3-6}$ alkyl alcohol, $C_{3-6}$ alkyl lactate and sodium chloride. If necessary, further $C_{3-6}$ alkyl alcohol (e.g. n-butanol) may also be added. $C_{3-6}$ alkyl lactate preferentially partitions into the alkyl alcohol phase and sodium chloride preferentially partitions into the aqueous phase, facilitating separation of sodium chloride and $C_{3-6}$ alkyl lactate by liquid-liquid phase separation. The conditions are controlled to ensure that hydrolysis of $C_{3-6}$ alkyl lactate does not occur to any appreciable extent, for example admixing of the esterification products with water and subsequent phase separation may be carried out at ambient temperature. Accordingly, in some preferred embodiments the process of the invention comprises: (a) reacting a stream rich in saccharide with sodium hydroxide in the presence of water to produce a reaction mixture comprising sodium lactate; (b) admixing at least a portion of the reaction mixture from step (a) with HCl and with $C_{3-6}$ alkyl alcohol to produce lactic acid and sodium chloride; (b") reacting at least a portion of the lactic acid with $C_{3-6}$ alkyl alcohol to produce the corresponding alkyl lactate; (b"') admixing the product mixture of step (b") and water to produce a biphasic mixture, and separating sodium chloride and $C_{3-6}$ alkyl lactate by liquid-liquid phase separation; (c)

converting at least a portion of the sodium chloride to chlorine and sodium hydroxide; and (d) recycling at least a portion of the sodium hydroxide produced in step (c) to step (a).

In another preferred embodiment, the process of the invention comprises: a) reacting a stream rich in saccharide with sodium hydroxide in the presence of water to produce a reaction mixture comprising sodium lactate; (b) reacting at least a portion of the sodium lactate with HCl to produce lactic acid and sodium chloride; (bb) reducing the volume of the reaction mixture obtained from step (b) by removal (e.g. evaporation) of water; (b") reacting at least a portion of the lactic acid with a $C_{1-6}$ alkyl alcohol to produce the corresponding alkyl lactate; (b''') separating solid sodium chloride from the $C_{1-6}$ alkyl lactate (e.g. by filtration); (c) converting at least a portion of the sodium chloride to chlorine and sodium hydroxide; and (d) recycling at least a portion of the sodium hydroxide produced in step (c) to step (a).

In step (c) at least a portion of the sodium chloride is converted to chlorine and sodium hydroxide. This may for example be carried out by electrolysis of aqueous sodium chloride to produce chlorine, sodium hydroxide and hydrogen. The reaction may be carried out using, for example, a diaphragm cell, a mercury cell or a membrane cell. In each case, the overall process reaction is: $2NaCl+2H_2O \rightarrow Cl_2+H_2+2NaOH$, with chlorine being produced at the positive electrode (anode), and sodium hydroxide and hydrogen (directly or indirectly) being produced at the negative electrode (cathode).

In a diaphragm cell, a porous diaphragm divides the electrolytic cell into anode compartments and cathode compartments. An aqueous solution containing sodium chloride is introduced into the anode compartment which may also flow through the diaphragm into the cathode compartment. When an electric current is applied to the aqueous sodium chloride solution, chlorine gas is produced at the anode, and hydrogen gas and sodium hydroxide are produced at the cathode (sodium ions are transported from the anode compartment to the cathode compartment where they combine with hydroxyl ions generated at the cathode). The diaphragm resists back-migration of hydroxyl ions, thereby preventing undesired reaction of chlorine produced at the anode with hydroxyl ions. An aqueous solution comprising sodium hydroxide (the solution typically also contains some sodium chloride) exits from the cathode compartment.

In a membrane cell, a selective ion-permeable membrane divides the electrolytic cell into anode compartments and cathode compartments. Again the feedstock is an aqueous solution containing sodium chloride. When an electric current is applied, chlorine is produced at the anode, and hydrogen gas and sodium hydroxide are produced at the cathode. The membrane permits passage of positively-charged sodium ions between compartments but prevents passage of negatively-charged hydroxide or chloride, thereby preventing undesired reaction of chlorine produced at the anode with hydroxide ions.

In a mercury cell, the electrolytic cell comprises a mercury cathode. Once again the feedstock is an aqueous solution containing sodium chloride. When an electric current is applied, chlorine is produced at the anode, with sodium being produced at the mercury cathode which forms a sodium-mercury amalgam. Reaction of the amalgam with water (typically in a decomposer) produces sodium hydroxide and hydrogen, regenerating mercury which may be recycled to the electrolytic cell.

By converting the sodium chloride obtained in step (b) to chlorine, hydrogen and sodium hydroxide in step (c), the process of the invention enables the recovery and recycling of many of the process inputs. For example, in step (d), at least a portion of the sodium hydroxide produced in step (c) is recycled to step (a) of the process, and is used to produce further sodium lactate from saccharide. Preferably, most or all of the sodium hydroxide produced in step (c) is recycled to step (a). The process of the invention also allows for recovery and/or regeneration of other process inputs. For example, where $C_{1-6}$ alkyl alcohol is used (e.g. as solvent and/or reagent for production of $C_{1-6}$ alkyl lactate), excess $C_{1-6}$ alkyl alcohol may be recovered by distillation and recycled to the process. In one preferred embodiment, where the process includes an esterification step (step (b")) in which a mixture of a mixture of water and $C_{3-6}$ alkyl alcohol is removed from the reaction mixture by evaporation, the process includes a decanting step (x) in which a condensed mixture of water and $C_{3-6}$ alkyl alcohol is separated into a $C_{3-6}$ alkyl alcohol stream and a water stream by decanting the upper alkyl alcohol phase and then draining the lower water phase. The $C_{3-6}$ alkyl alcohol and/or the water streams may optionally be further purified (e.g. by distillation), and recycled to the process. Water streams obtained by such processes will typically contain HCl and be acidic.

In addition, chlorine produced in step (c) of the process may be reacted with hydrogen produced in step (c) of the process to produce HCl. The HCl may then be recycled to step (b) of the process if desired. The reaction of hydrogen with chlorine is exothermic, and is typically carried out in a suitable graphite combustion chamber using a suitable ignition source. The hydrogen chloride generated is typically contacted with water, to produce HCl in the form of aqueous hydrochloric acid. In a preferred embodiment, an integrated chlorine burner/HCl absorber is used. In a preferred embodiment, at least a portion of the chlorine produced in step (c) is reacted with hydrogen to produce HCl. Preferably most or all of the chlorine produced in step (c) is reacted with hydrogen.

As discussed above, HCl produced by reaction of hydrogen with chlorine may be recycled to step (b) of the process if desired. Accordingly, in a preferred embodiment, at least a portion of the HCl is recycled to step (b) of the process, and is used to produce further lactic acid and sodium chloride. Preferably most or all of the HCl is recycled to step (b). It will be appreciated that the ability to regenerate and recycle many of the process inputs depends on the particular choice of sodium hydroxide as the base used in step (a), the choice of HCl as the acid used in step (b), and the conversion of sodium chloride to chlorine, hydrogen and sodium hydroxide in step (c).

It will further be appreciated that certain features of the processes described herein are particularly advantageous. As discussed above, the use of $C_{3-6}$ alkyl alcohols, and in particular n-butanol, is preferred since in the presence of sodium chloride, lactic acid and water, a biphasic mixture is produced. The use of a $C_{3-6}$ alkyl alcohol, such as n-butanol, enables separation of sodium chloride from lactic acid by liquid-liquid phase separation, facilitating good recovery of lactic acid and reducing the need for energy-intensive distillation/evaporation processes. Accordingly, in a second aspect, the invention provides a process for the production of lactic acid or $C_{3-6}$ alkyl lactate comprising: (a) reacting a stream rich in saccharide with sodium hydroxide in the presence of water to produce a reaction mixture comprising sodium lactate; (b) admixing at least a portion of the sodium lactate and water with HCl and with $C_{3-6}$ alkyl alcohol to produce a biphasic mixture comprising lactic acid and sodium chloride; (b') separating sodium chloride and water from lactic acid by liquid-liquid phase separation; and optionally (b''') reacting at least a portion of the lactic acid with $C_{3-6}$ alkyl alcohol to produce $C_{3-6}$ alkyl lactate. The preferences described above for the first aspect of the invention in relation to step (a) (for features such as saccharide, solvent, ratio of water to saccharide, ratio of sodium hydroxide to saccharide, temperature, addition time, concentration, and removal of water), step (b) (for features such as the form of HCl, temperature, ratio of sodium lactate to HCl, ratio of sodium hydroxide to HCl, alkyl alcohol, and ratio of alkyl alcohol to water) and step (b''') (for features such as the acid catalyst, temperature, and solvent) are also applicable to the second aspect of the invention. In a particularly preferred embodiment, the $C_{3-6}$ alkyl alcohol is n-butanol.

In a third aspect, the invention provides a process for the production of a $C_{1-6}$ alkyl lactate comprising: (a) reacting a stream rich in saccharide with sodium hydroxide in the presence of water to produce a reaction mixture comprising sodium lactate; (b) admixing at least a portion of the sodium lactate with HCl and with a $C_{1-6}$ alkyl alcohol to produce lactic acid and sodium chloride; (b''') reacting at least a portion of the lactic acid with the $C_{1-6}$ alkyl alcohol to produce the corresponding alkyl lactate; and (b'''') separating sodium chloride and $C_{1-6}$ alkyl lactate. The preferences described above for the first aspect of the invention in relation to step (a) (for features such as saccharide, solvent, ratio of water to saccharide, ratio of sodium hydroxide to saccharide, temperature, addition time, and concentration), step (b) (for features such as the form of HCl, temperature, ratio of sodium lactate to HCl, ratio of sodium hydroxide to HCl, alkyl alcohol, and ratio of alkyl alcohol to water), step (b''') (for features such as alkyl alcohol, acid catalyst, temperature, and solvent) and step (b'''') (for features such as the mode of separation of sodium chloride) are also applicable to the third aspect of the invention. Preferably the $C_{1-6}$ alkyl alcohol is a $C_{3-6}$ alkyl alcohol, more preferably n-butanol. Preferably, following step (b) but prior to step (b'''), the process includes (bb) reducing the volume of the reaction mixture obtained from step (b) by removal (e.g. evaporation) of water.

In a particularly preferred embodiment of the first aspect of the invention, the process comprises:
(a) reacting a stream rich in saccharide with sodium hydroxide in the presence of water to produce a reaction mixture comprising sodium lactate;
(b) reacting at least a portion of the sodium lactate with HCl to produce lactic acid and sodium chloride;
(b''') reacting at least a portion of the lactic acid with a $C_{1-6}$ alkyl alcohol (preferably n-butanol) to produce the corresponding alkyl lactate;
(c) converting at least a portion of the sodium chloride to chlorine and sodium hydroxide;
(d) recycling at least a portion of the sodium hydroxide produced in step (c) to step (a);
(e) reacting at least a portion of the chlorine produced in step (c) with hydrogen to produce HCl; and
(f) recycling at least a portion of the HCl produced in step (e) to step (b).

In a particularly preferred embodiment of the first aspect of the invention, the process comprises:
(a) reacting a stream rich in saccharide with sodium hydroxide in the presence of water to produce a reaction mixture comprising sodium lactate;
(b) reacting at least a portion of the sodium lactate with HCl to produce lactic acid and sodium chloride;
(b''') reacting at least a portion of the lactic acid with a $C_{1-6}$ alkyl alcohol (preferably n-butanol) to produce the corresponding alkyl lactate;
(b'''') separating solid sodium chloride from the $C_{1-6}$ alkyl lactate (e.g. by filtration);
(c) converting at least a portion of the sodium chloride to chlorine and sodium hydroxide;
(d) recycling at least a portion of the sodium hydroxide produced in step (c) to step (a);
(e) reacting at least a portion of the chlorine produced in step (c) with hydrogen to produce HCl; and
(f) recycling at least a portion of the HCl produced in step (e) to step (b).

The processes of the invention may be carried out under ambient or inert atmospheres. For example, the process may be carried out using equipment that is open to the air, or may be carried out under a nitrogen or argon atmosphere. It may be carried out in a batch, fed-batch, semi-continuous or continuous process, and the various products of the process of the invention may be subject to any desired purification and/or additional processing steps. For example, where $C_{1-6}$ alkyl lactate is produced, it may be recovered by distillation, e.g. distillation under reduced pressure.

Accordingly, in a particularly preferred embodiment of the first aspect of the invention, the process comprises:
(a) reacting a stream rich in saccharide with sodium hydroxide in the presence of water to produce a reaction mixture comprising sodium lactate;
(b) reacting at least a portion of the sodium lactate with HCl to produce lactic acid and sodium chloride;
(bb) reducing the volume of the reaction mixture obtained from step (b) by removal (e.g. evaporation) of water;
(b''') reacting at least a portion of the lactic acid with a $C_{1-6}$ alkyl alcohol (preferably n-butanol) to produce the corresponding alkyl lactate;
(b'''') separating solid sodium chloride from the $C_{1-6}$ alkyl lactate (e.g. by filtration);
(b''''') purifying the $C_{1-6}$ alkyl lactate by distillation;
(c) converting at least a portion of the sodium chloride to chlorine and sodium hydroxide;
(d) recycling at least a portion of the sodium hydroxide produced in step (c) to step (a);
(e) reacting at least a portion of the chlorine produced in step (c) with hydrogen to produce HCl; and
(f) recycling at least a portion of the HCl produced in step (e) to step (b).

In step (a), reaction of sodium hydroxide with saccharide leads to the production of sodium salts of other organic acids in addition to sodium lactate. Where the process of the invention includes an esterification step, $C_{1-6}$ alkyl esters of those organic acids will typically be produced together with $C_{1-6}$ alkyl lactate. Typically, some of the byproducts present in the mixture obtained from the esterification step will have low boiling points (i.e. lower than the boiling point of the $C_{1-6}$ alkyl lactate), and some of the byproducts will have high boiling points (i.e. higher than the boiling point of the $C_{1-6}$ alkyl lactate) or will be non-volatile. Accordingly, where the process of the invention includes an esterification step (step (b''')), the process preferably also includes a multi-stage distillation process in which:
1) the mixture obtained following step (b''') or, where sodium chloride is separated from $C_{1-6}$ alkyl lactate, following step (b''''), is introduced to a first distillation column and the mixture is distilled so as to obtain i) a first light fraction comprising $C_{1-6}$ alkyl alcohol and one or more byproducts having high boiling points, said byproducts including at least one $C_{1-6}$ alkyl ester of an organic acid other than lactic acid, and ii) a first heavy fraction comprising $C_{1-6}$ alkyl lactate and one or more byproducts which have low boiling points or which are non-volatile; and 2) the first heavy fraction is introduced to a second distillation column and the mixture is distilled so as to obtain i) a second light fraction comprising $C_{1-6}$ alkyl lactate; and ii) a second heavy fraction comprising one or more byproducts which have low boiling points or which are non-volatile. In such embodiments, the alkyl alcohol is preferably n-butanol and the alkyl esters are preferably n-butyl esters.

In such embodiments, the alkyl alcohol (preferably n-butanol) present in the esters of other organic acids may also be recovered and recycled to the process. For example, where the first light fraction obtained from the first distillation column comprises $C_{3-6}$ alkyl alcohol and $C_{3-6}$ alkyl esters of organic acids other than lactic acid, the process may comprise a hydrolysis step (y) in which the first light fraction is admixed with excess acidic water (e.g. acidic water obtained from decanting step (x)) and heated so as to hydrolyse said $C_{3-6}$ alkyl esters, resulting in the production of organic acids and $C_{3-6}$ alkyl alcohol. During the hydrolysis step, a mixture of acidic water and alkyl alcohol is removed from the mixture by evaporation. A stream containing a mixture of acidic water and $C_{3-6}$ alkyl alcohol removed from a hydrolysis reaction mixture during hydrolysis step (y) may optionally be combined with a stream containing a mixture of mixture of water and $C_{3-6}$ alkyl alcohol removed from an esterification mixture during esterification step (b"), the organic and aqueous layers separated by decanting as described above for step (x), and the $C_{3-6}$ alkyl alcohol and/or acidic water recycled to the process.

The lactic acid or $C_{1-6}$ alkyl lactate produced by the process of the invention may be converted into further useful downstream products by routine methods. Accordingly, the invention also provides a process for the production of oligomeric lactic acid, lactide, alkyl lactyllactate or poly-lactic acid comprising producing lactic acid or a $C_{1-6}$ alkyl lactate by a process according to the invention; and converting said lactic acid or $C_{1-6}$ alkyl lactate into oligomeric lactic acid, lactide, alkyl lactyllactate or poly-lactic acid. For example oligomeric lactic acid may be produced by heating lactic acid or $C_{1-6}$ alkyl lactate with removal of water or alkyl alcohol as required. Lactide may be produced for example by converting lactic acid or $C_{1-6}$ alkyl lactate into oligomeric lactic acid, and heating the oligomeric lactic acid in the presence of a transesterification catalyst. Alkyl lactyllactate may for example be produced for example by converting lactic acid or $C_{1-6}$ alkyl lactate into lactide, and by reacting lactide with an alkyl alcohol under appropriate conditions. Poly-lactic acid may for example be produced by converting lactic acid or $C_{1-6}$ alkyl lactate into lactide, and polymerising the lactide to produce poly-lactic acid. The lactic acid or $C_{1-6}$ alkyl lactate may also be converted to propylene glycol (1,2-propanediol), for example by hydrogenation using a metal catalyst (e.g. a ruthenium, rhenium or copper-containing catalyst). The lactic acid or $C_{1-6}$ alkyl lactate may also be converted to acrylic acid, using, for example phosphate, sulfate, zeolite or clay catalysts.

Particularly preferred embodiments of the first aspect of the invention are shown in the figures. In the embodiment shown in FIG. 1, a solution containing saccharide (e.g. xylose, glucose) in water 1 is admixed with a solution of sodium hydroxide in water 2 in reactor 30 with agitation at elevated temperature, resulting in the production of sodium lactate (together with sodium salts of other organic acids). The products are exited from reactor as stream 11 and are fed into an integrated chlorine burner/HCl absorber 31. Other inputs to chlorine burner/HCl absorber 31 include a chlorine stream 3 and a hydrogen stream 4. Within the chlorine burner/HCl absorber 31, chlorine and hydrogen is burned to produce HCl gas, which is then absorbed by water. The HCl produced is reacted with sodium lactate (and sodium salts of other organic acids) resulting in the production of an aqueous product stream 12 containing lactic acid, other organic acids, and sodium chloride. Stream 12 is then fed into evaporator 32 and the volume of the mixture is reduced by removal of some of the water 7 by evaporation. The resulting concentrated mixture 13 is then introduced to an esterification reactor 33, where it is admixed with n-butanol 5. If desired, prior to introduction of concentrated mixture 13 to esterification reactor 33, additional HCl 6 may be added to the concentrated mixture. Upon admixing of the concentrated mixture and n-butanol in esterification reactor 33, solid sodium chloride precipitates. The mixture in esterification reactor 33 is heated with agitation and water and n-butanol 24 are removed by evaporation. As the proportion of water decreases and the proportion of n-butanol increases, lactic acid is converted to n-butyl lactate. Similarly, other organic acids are converted to their n-butyl esters. Additionally, as the proportion of water decreases and the proportion of n-butanol increases, further solid sodium chloride is formed. If desired, additional n-butanol may be added to reactor 33 during the esterification reaction. The product mixture 14 exiting esterification reactor 33 contains n-butyl lactate, n-butyl esters of other organic acids, n-butanol and solid sodium chloride.

Figure 2:
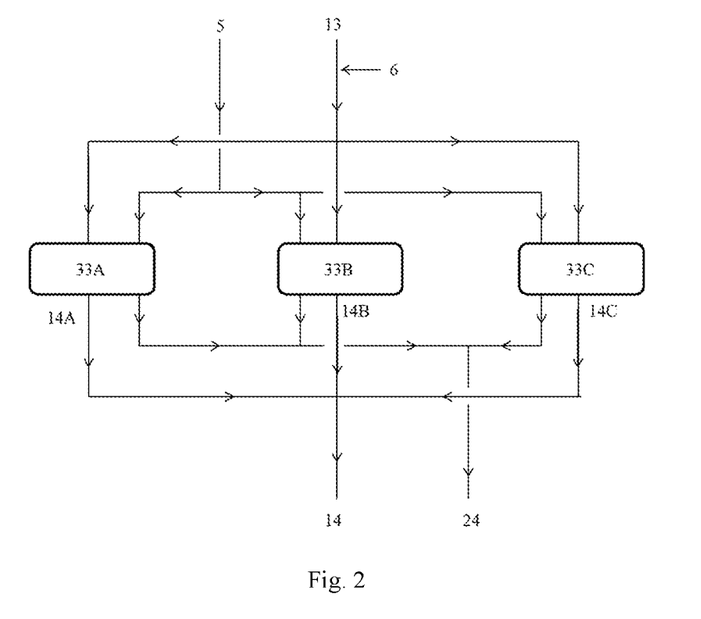
FIG. 2 shows a variant of part of the embodiment shown in FIG. 1 in which, instead of a single esterification reactor, a plurality of esterification reactors are used in parallel.
Figure 3:
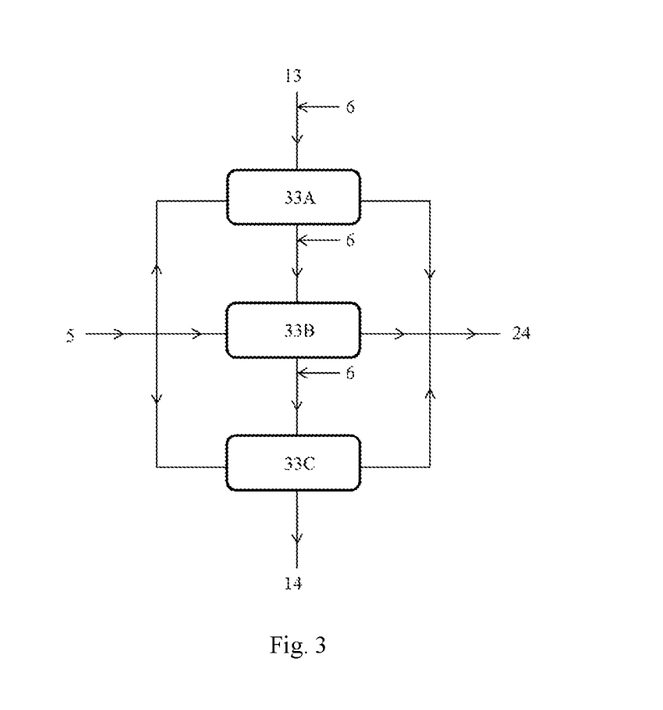
FIG. 3 shows a variant of part of the embodiment shown in FIG. 1 in which, instead of a single esterification reactor, a plurality of esterification reactors are used in series.

In some embodiments, a plurality of esterification reactors may be used. For example, the concentrated mixture 13 may be admixed with aqueous hydrochloric acid 6, and then portions of the mixture introduced to different esterification reactors operating in parallel (e.g. esterification reactors 33A, 33B and 33C, as shown in FIG. 2) and admixed with n-butanol to produce n-butyl lactate. The resulting streams 14A, 14B and 14C (which contain n-butyl lactate, n-butyl esters of other organic acids, n-butanol and solid sodium chloride) may then be combined for further processing. Alternatively, a plurality of esterification reactors operating in series may be used (see FIG. 3). For example, the concentrated mixture 13 may be admixed with aqueous hydrochloric acid, and then the mixture introduced to esterification reactor 33A where it is admixed with n-butanol 5. Following heating and removal of some water and n-butanol, the partially esterified mixture may be passed to esterification reactor 33B where it is admixed with further n-butanol 5, and optionally further hydrochloric acid. The mixture is heated with removal of some water and n-butanol 24, and the partially esterified mixture may then be passed to esterification reactor 33C where it is admixed with further n-butanol 5, and optionally further hydrochloric acid 6. The mixture is again heated with removal of water and n-butanol 24, until esterification is complete. Stream 14 exits esterification reactor 33C and is taken on for further processing.

Figure 1:
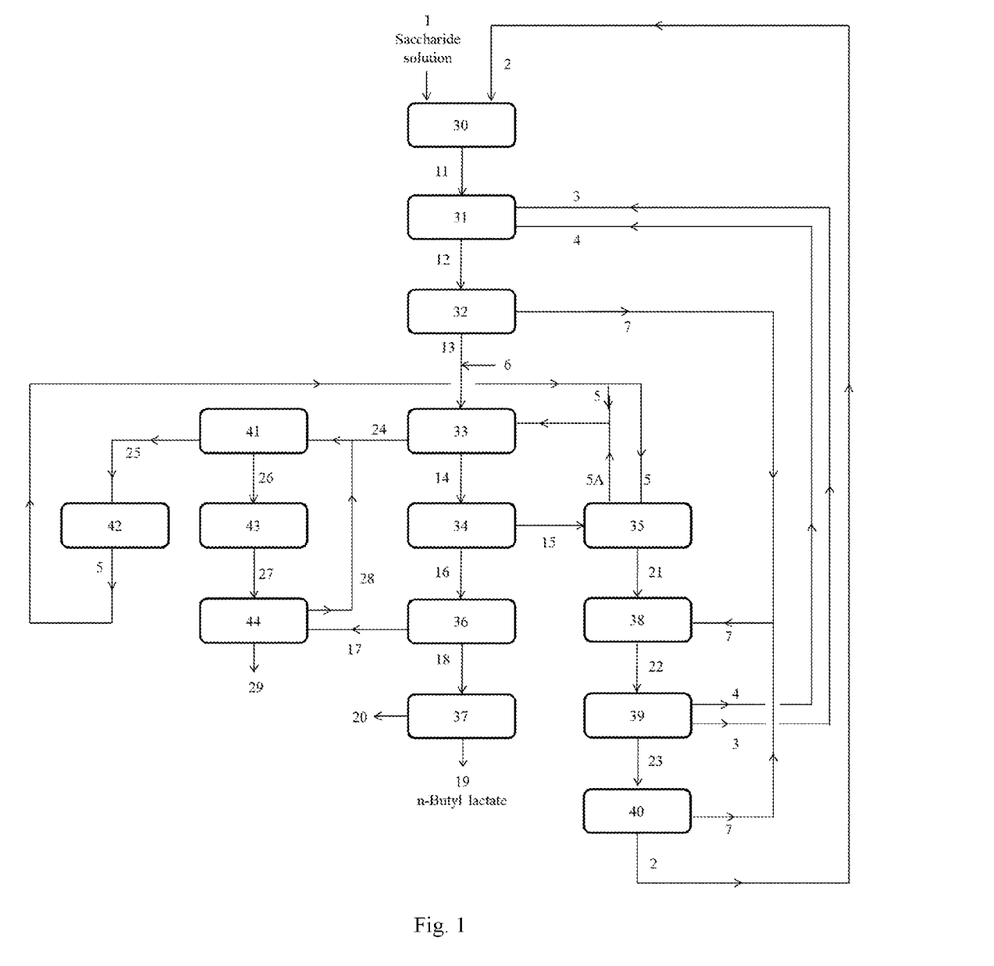
FIG. 1 shows a preferred embodiment of the process of the invention.

Product stream 14 containing n-butyl lactate, n-butyl esters of other organic acids, n-butanol and solid sodium chloride is passed to filtration unit 34 where the solid sodium chloride 15 is separated from the liquid components (i.e. n-butyl lactate, n-butyl esters of other organic acids and n-butanol) 16. The solid sodium chloride is then passed to a further filtration unit 35 where it is washed with n-butanol 5. The n-butanol washings 5A may be introduced to esterification reactor 33 and re-used in the process.

The liquid components from the initial filtration step 16 are introduced as a feed stream to a first distillation column 36. Heating is applied so as to obtain a light fraction 17 (containing n-butanol and other low boiling impurities including n-butyl esters of some other organic acids) and a heavy fraction 18 (containing n-butyl lactate and other high boiling impurities) are obtained. The heavy fraction 18 is introduced to a second distillation column 37 and heating is applied so as to obtain a light fraction 19 containing purified n-butyl lactate and a heavy fraction 20 containing other impurities.

The washed solid sodium chloride 21 is then admixed with water 7 in brine vessel 38 with agitation. The resulting brine solution 22 is then passed to a brine electrolysis unit 39. On application of an electric current, chlorine gas 3, hydrogen gas 4 and dilute aqueous sodium hydroxide streams 23 are produced. The chlorine and hydrogen streams 3 and 4 are fed into chlorine burner/HCl absorber 31, and recycled to the process. The dilute aqueous sodium hydroxide stream 23 is fed to an evaporator 40, and the volume of the mixture is reduced by removal of some of the water 7 by evaporation, resulting in production of a concentrated aqueous sodium hydroxide stream 2. The aqueous sodium hydroxide 2 is admixed with saccharide solution 1 in reactor 30, and so is also recycled to the process. The water may also be recycled, e.g. by re-introduction into brine vessel 38.

As discussed above, during the esterification reaction n-butanol and water are removed by evaporation. Following condensation of the combined n-butanol and water stream 24, liquid n-butanol and water (which contains some HCl and is acidic) are introduced to decanter vessel 41, separate n-butanol and water phases are obtained, and separate n-butanol 25 and water 26 treams are obtained. The n-butanol and water streams are purified separately by distillation using distillation columns 42 and 43, to obtain purified n-butanol 5 and acidic water 27.

n-Butanol is also recovered from the n-butyl esters of other organic acids which are formed during the esterification reaction. Light fraction 17 obtained from the first distillation column and an excess of acidic water 27 are admixed in hydrolysis column 44 at elevated temperature, resulting in the production of organic acids and n-butanol. Water and n-butanol are removed by evaporation, and the n-butanol/water stream 28 is combined with n-butanol/water stream 24. An aqueous mixture of the other organic acids 29 is also obtained.

As discussed above, if desired the purified n-butyl lactate 19 may be hydrolysed to produce lactic acid, for example by heating the n-butyl lactate in the presence of excess water in the presence of an acid catalyst (e.g. HCl, lactic acid). The purified n-butyl lactate or the lactic acid may also be converted to other products such as oligomeric lactic acid, lactide, or polylactic acid. In addition, the purified n-butyl lactate or the lactic acid may be converted to propylene glycol (1,2-propanediol), for example by hydrogenation using a metal catalyst (e.g. a ruthenium, rhenium or copper-containing catalyst).

The following examples illustrate the invention.

Example 1

Preparation of Lactic Acid and Conversion into Alkyl Lactate with Separation of Sodium Chloride A solution of D-xylose (200.1 g in 300 g water; 40% w/w) and a solution of NaOH (215.1 g in 385 g water; 4.0 equivalents) were added dropwise to a jacketed 60 mL capacity continuous stirred-tank reactor (CSTR), fitted with an overhead stirrer and thermocouple/reflux condenser and a charge port heated with an oil jacket temperature of c. 120° C. The addition was made over a period of 4 hrs (with mean CSTR residence time of c. 15 min) and upon egress from the CSTR, the product mixture was collected in a 1000 mL bottle. Once the final feed additions were complete, the residual reaction mixture was discharged, yielding ~870 mL/1086 g of product.

31.1 g of this reaction mixture was weighed into a 50 mL conical flask. 15.8 g concentrated aqueous hydrochloric acid (37%) was added drop-wise to form a clear, brown solution of c. pH 1. This clear solution was then added drop-wise, using a peristaltic pump, into another flask (250 mL round-bottom flask fitted with a magnetic follower stirrer (750 rpm), thermocouple, Dean-Stark trap/reflux condenser and $N_2$ bleed) containing refluxing n-butanol (100 mL, pot temperature 119° C.). The addition period was 2 hours, during which water was continuously removed. During the addition, simultaneous precipitation of sodium chloride was also observed. Upon completion of the addition, the mixture was maintained at reflux until no further water was collected in the trap (2 hours). A total of 35 mL water was collected. The reaction mixture was then allowed to cool to ambient temperature (25-30° C.) and the precipitate was filtered off.

The yield of n-butyl lactate in the n-butanol filtrate was determined to be 37.2% by gas chromatography, consistent with a quantitative conversion of sodium lactate into n-butyl lactate.

The sodium chloride removed in the filtration step was dried and found to weigh 8.6 g, a recovery efficiency of 96%. The n-butanol filtrate was analysed by flame photometry and no residual sodium ions were detected.

Example 2

Preparation of Lactic Acid with Separation of Alkyl Lactate

A solution of D-xylose (200.2 g in 300 g water; 40% w/w) and a solution of NaOH (110.1 g in 390 g water; 2.0 equivalents) were added dropwise to a jacketed 60 mL capacity continuous stirred-tank reactor (CSTR), fitted with an overhead stirrer and thermocouple/reflux condenser and a charge port heated with an oil jacket temperature of c. 120° C. The addition was made over a period of 4 hours (with mean CSTR residence time of c. 15 min) and upon egress from the CSTR, the product mixture was collected in a 1000 mL bottle. Once the final feed additions were complete, the residual reaction mixture was discharged, yielding ~860 mL/990.1 g of product.

The lactate selectivity for this reaction mixture was determined by reverse-phase HPLC to be 32.2%.

A 31.2 g (27.0 mL) portion of this solution was added to a 250 mL round-bottomed reaction flask, and 8.61 g HCl (37% in water) was added dropwise with stirring to generate a solution of pH 1. 100 mL (79.7 g) of n-butanol was added to the mixture and stirring (400 rpm) proceeded for 150 minutes at room temperature (24° C.). After stirring was complete, the flask contents were transferred to a 500 mL separating funnel and the layers allowed to fully separate on standing. The lower, pale yellow, clear aqueous layer was carefully removed in to a glass sample jar and had a volume of 23 mL, weight of 26.1 g. The upper, dark brown, clear n-butanol layer was then poured in to a separate glass jar and had a volume of 111 mL, 93.2 g.

The aqueous and butanol layers in their entirety were each added carefully to separate 1000 mL volumetric flasks, acidified with 2 mL HCl to ensure the pH was 1 and made up to volume with deionised water. After mixing well, a portion of each was analysed by HPLC (C18 Column) for lactic acid content in each layer.

The theoretical lactic acid yield from the xylose/sodium hydroxide solution, at the weight taken, was 1.74 g. This was based on an overall selectivity of 32.2% from the initial base degradation reaction. The lactic acid in the n-butanol layer was 1.50 g, giving a yield of 83.1%.

The sodium content of the aqueous layer was measured by flame photometry to correspond to 96% of the anticipated total.

Example 3

Preparation of Lactic Acid and Conversion into Alkyl Lactate with Separation of Sodium Hydroxide A solution of D-xylose (200.1 g in 300 g water; 40% w/w) and a solution of NaOH (215.1 g in 385 g water; 4.0 equivalents) were added dropwise to a jacketed 60 mL capacity continuous stirred-tank reactor (CSTR), fitted with an overhead stirrer and thermocouple/reflux condenser and a charge port heated with an oil jacket temperature of c. 120° C. The addition was made over a period of 4 hours (with mean CSTR residence time of c. 15 min) and upon egress from the CSTR, the product mixture was collected in a 1000 mL bottle. Once the final feed additions were complete, the residual reaction mixture was discharged, yielding ~870 mL/1086 g of product.

The lactate selectivity for this reaction mixture was determined by reverse-phase HPLC to be 37.1%

30.9 g of this reaction mixture (containing 0.038 moles xylose and 0.15 moles sodium, based on initial charge) was weighed into a 50 mL conical flask. 15.8 g (4.2 equivalents on xylose) concentrated aqueous hydrochloric acid (37%) was added drop-wise to form a clear, brown solution (pH ~1). This clear solution was then added drop-wise, using a peristaltic pump, into another flask (250 mL round-bottom flask fitted with a magnetic follower stirrer (750 rpm), thermocouple, Dean-Stark trap/reflux condenser and $N_2$ bleed) containing refluxing n-butanol (100 mL, pot temperature 119° C.). The addition period was 2 hours, during which water was continuously removed and the pot temperature varied between from 119-106-119° C. During the addition, simultaneous precipitation of sodium chloride was also observed. Upon completion of the addition, the mixture was maintained at reflux until no further water was collected in the trap (2 hours). A total of 35 mL water was collected. The reaction mixture was then allowed to cool to ambient temperature (25-30° C.).

24.9 mL demineralised water (the amount of water required to form a saturated brine solution based on the theoretical NaCl content, i.e. 8.96 g) was syringed into the reaction flask and the mixture was stirred at ambient temperature for 1 hour. This mixture was then transferred to a 250 mL separating funnel and the two phases allowed to separate on standing. The lower, aqueous layer was carefully removed (25 mL). The separating funnel was rinsed with ~10 mL n-butanol and the respective aqueous and organic layers were combined with their bulk counterparts. The organic layer(s) were made-up to 250 mL in a volumetric flask with n-butanol and this was analysed for racemic n-butyl lactate, by gas chromatography. The yield of racemic n-butyl lactate was calculated as 35.6% (c.f. 37.1% after stage (a); 96% lactate recovery), and the sodium recovery in the aqueous layer (measured by $Na^+$ flame photometry) was calculated to be 3.49 (±0.25) g, (99%).

Example 4

Production of Lactic Acid with Recovery and Recycle of Sodium Hydroxide

A solution of 40% w/w xylose is prepared by adding 200 g D-xylose and 300 g demineralised water to a 500 mL conical flask. This is mixed, with the aid of a sonicating bath, until a clear solution is formed.

A solution containing two molar equivalents of sodium hydroxide (based on the xylose charge above) is prepared by weighing 110 g sodium hydroxide pellets into a 500 mL conical flask and carefully adding 390 g demineralised water. This is mixed, with cooling, until a clear solution is formed.

The xylose and sodium hydroxide solutions are then added to a heated (oil jacket temperature ~120° C.), ~60 mL continuous stirred-tank reactor (CSTR), fitted with an overhead stirrer, thermocouple/reflux condenser and a charge port. Addition is made over a period of 4 hours (reaction residence time ~15 min), using a peristaltic pump, maintaining the reaction temperature in the range of from 100-105° C. Upon egress from the CSTR, reaction mixture containing sodium lactate is collected. Once the final feed additions are complete, the residual reaction mixture is discharged.

A 31 g (27 mL) portion of this solution is added to a 250 mL round-bottomed reaction flask with a magnetic stirrer follower, and 8.6 g HCl (37% in water) is added dropwise.

100 mL (80 g) of n-butanol is added to the mixture, which is then stirred (400 rpm) for 150 minutes at room temperature (24° C.).

After stirring is complete, the flask contents are transferred to a 500 mL separating funnel and the layers are allowed to fully separate on standing. The lower aqueous layer, which contains sodium chloride, is removed and collected in a suitable flask. The upper organic layer contains lactic acid.

The aqueous sodium chloride solution is introduced into an electrolytic cell having a selectively ion-permeable membrane dividing the cell into anode and cathode compartments. An electric current is applied to the cell resulting in production of chlorine at the anode and production of hydrogen gas and sodium hydroxide at the cathode.

Aqueous sodium hydroxide solution is recovered from the cell, and concentrated to a sodium hydroxide concentration of 22% w/w.

The resulting aqueous sodium hydroxide solution, and an aqueous 40% w/w D-xylose solution, are admixed in the CSTR reaction vessel described above with stirring over time at a temperature in the range of from 100-105° C., resulting in the production of further sodium lactate.

Example 5

Fed Batch Preparation of Lactic Acid and Conversion into Alkyl Lactate with Separation of Sodium Chloride A 5 L round bottomed flask equipped with an overhead stirrer, reflux condenser, temperature probe and inlet for sugar feed, was charged with 640 g water. Sodium hydroxide pellets (426.7 g, 10.67 moles) were added in portions to form a 40% w/w NaOH solution. A separate 5 L round bottomed flask equipped with an overhead stirrer was charged with 1,200 g water, followed by 800 g xylose (5.33 moles, 0.50 equivalents with respect to NaOH) in portions to form a 40% w/w xylose solution.

The 40% w/w sodium hydroxide solution was heated to 100-105° C. and then the 40% w/w xylose solution was fed into the hot sodium hydroxide solution over a period of either 15 or 60 minutes using a peristaltic pump. Upon completion of the addition of xylose the reaction was cooled to ambient temperate and a sample (~5 mL) was analysed for lactic acid content by HPLC.

In situ yields of lactic acid at this point were typically found to be 41-44% with 15 minute addition periods giving yields at the lower end of the range (41-42%) and 60 minute addition periods giving yields at the higher end (43-44%).

The remaining reaction solution was acidified with concentrated HCl (37%, 920.6 mL, 0.5 equivalents to NaOH) and divided into two equal portions. The acidified mixtures were each fed over 8 hours, using peristaltic pumps, into 5 L round bottomed flasks containing refluxing n-butanol (3 L in each) and set-up for azeotropic water removal by means of a Dean-Stark apparatus. Upon completion of the addition the reaction was refluxed for a further 8 hours until no water was observed in the Dean-Stark trap. The reaction mixtures were then cooled and precipitated sodium chloride was filtered and washed with n-butanol (2×100 mL). The filtrate was analysed by gas chromatography for n-butyl lactate content and the sodium chloride was dried in an oven. The results indicated complete conversion of the lactic acid to n-butyl lactate. NaCl recovery was >98% by weight.

Example 6

Production of Lactic Acid and Conversion into Alkyl Lactate with Recovery and Recycle of Sodium Hydroxide A 5 L round bottomed flask equipped with an overhead stirrer, reflux condenser, temperature probe and inlet for sugar feed, is charged with 640 g water. Sodium hydroxide pellets (426.7 g, 10.67 moles) are added in portions to form a 40% w/w NaOH solution. A separate 5 L round bottomed flask equipped with an overhead stirrer is charged with 1,200 g water, followed by 800 g xylose (5.33 moles, 0.50 equivalents with respect to NaOH) in portions to form a 40% w/w xylose solution.

The 40% w/w sodium hydroxide solution is heated to 100-105° C. and then the 40% w/w xylose solution is fed into the hot sodium hydroxide solution over a period of 60 minutes using a peristaltic pump. Upon completion of the addition of xylose the sodium lactate-containing reaction mixture is cooled to ambient temperate.

The reaction solution is acidified with concentrated HCl (37%, 920.6 mL, 0.5 equivalents to NaOH) and divided into two equal portions. The acidified mixtures are each fed over 8 hours, using peristaltic pumps, into 5 L round bottomed flasks containing refluxing n-butanol (3 L in each) and set-up for azeotropic water removal by means of a Dean-Stark apparatus. Upon completion of the addition the reaction is refluxed until no further water is observed in the Dean-Stark trap. The reaction mixtures are then cooled and filtered to separate the liquid n-butyl lactate-containing phase from solid sodium chloride. The solid sodium chloride is washed with n-butanol (2×100 mL).

The solid sodium chloride is dissolved in water and the aqueous sodium chloride solution is introduced into an electrolytic cell having a selectively ion-permeable membrane dividing the cell into anode and cathode compartments. An electric current is applied to the cell resulting in production of chlorine at the anode and production of hydrogen gas and sodium hydroxide at the cathode.

Aqueous sodium hydroxide solution is recovered from the cell, and concentrated to a sodium hydroxide concentration of 40% w/w.

The resulting aqueous sodium hydroxide solution is fed to a 5 L round bottomed flask equipped with an overhead stirrer, reflux condenser, temperature probe and inlet for sugar feed, heated to 100-105° C. A further batch of 40% w/w aqueous xylose solution is then fed into the hot sodium hydroxide solution over a period of 60 minutes using a peristaltic pump, resulting in the production of further sodium lactate.

The invention claimed is:

1. A process for the production of lactic acid comprising:
    (a) reacting a stream rich in saccharide with sodium hydroxide in the presence of water to produce a reaction mixture comprising sodium lactate;
    (b) reacting at least a portion of the sodium lactate with HCl to produce lactic acid and sodium chloride;
    (c) converting at least a portion of the sodium chloride to chlorine and sodium hydroxide; and
    (d) recycling at least a portion of the sodium hydroxide produced in step (c) to step (a).

2. A process as claimed in claim 1, wherein the stream rich in saccharide is a stream rich in monosaccharide.

3. A process as claimed in claim 1, wherein the stream rich in saccharide is reacted with sodium hydroxide at a temperature in the range of from 10 to 160° C.

4. A process as claimed in claim 1, wherein the molar ratio of sodium hydroxide to saccharide, calculated as monosaccharide, is in the range of from 1.5:1 to 6:1.

5. A process as claimed in claim 1, wherein step (b) comprises admixing at least a portion of the reaction mixture from step (a) with HCl and with a $C_{3-6}$ alkyl alcohol to produce a biphasic mixture comprising lactic acid and sodium chloride.

6. A process as claimed in claim 5, wherein following step (b), sodium chloride and water are separated from lactic acid by liquid-liquid phase separation.

7. A process as claimed in claim 5, wherein the $C_{3-6}$ alkyl alcohol is n-butanol.

8. A process as claimed in claim 1, additionally comprising reacting at least a portion of the lactic acid with a $C_{1-6}$ alkyl alcohol to produce the corresponding $C_{1-6}$ alkyl lactate.

9. A process as claimed in claim 8, wherein the $C_{1-6}$ alkyl alcohol is n-butanol.

10. A process as claimed in claim 1, wherein at least a portion of the chlorine produced in step (c) is reacted with hydrogen to produce HCl.

11. A process as claimed in claim 10, wherein at least a portion of the HCl is recycled to step (b).

12. A process as claimed in claim 8, wherein the process comprises:
    (a) reacting a stream rich in saccharide with sodium hydroxide in the presence of water to produce a reaction mixture comprising sodium lactate;
    (b) reacting at least a portion of the sodium lactate with HCl to produce lactic acid and sodium chloride;
    (b") reacting at least a portion of the lactic acid with a $C_{1-6}$ alkyl alcohol to produce the corresponding alkyl lactate;

(b''') separating solid sodium chloride from the $C_{1-6}$ alkyl lactate;
(c) converting at least a portion of the sodium chloride to chlorine and sodium hydroxide;
(d) recycling at least a portion of the sodium hydroxide produced in step (c) to step (a);
(e) reacting at least a portion of the chlorine produced in step (c) with hydrogen to produce HCl; and
(f) recycling at least a portion of the HCl produced in step (e) to step (b).

13. A process as claimed in claim 8, wherein the process comprises:
    (a) reacting a stream rich in saccharide with sodium hydroxide in the presence of water to produce a reaction mixture comprising sodium lactate;
    (b) reacting at least a portion of the sodium lactate with HCl to produce lactic acid and sodium chloride;
    (bb) reducing the volume of the reaction mixture obtained from step (b) by removal of water;
    (b'') reacting at least a portion of the lactic acid with a $C_{1-6}$ alkyl alcohol to produce the corresponding alkyl lactate;
    (b''') separating solid sodium chloride from the $C_{1-6}$ alkyl lactate;
    (b'''') purifying the $C_{1-6}$ alkyl lactate by distillation;
    (c) converting at least a portion of the sodium chloride to chlorine and sodium hydroxide;
    (d) recycling at least a portion of the sodium hydroxide produced in step (c) to step (a);
    (e) reacting at least a portion of the chlorine produced in step (c) with hydrogen to produce HCl; and
    (f) recycling at least a portion of the HCl produced in step (e) to step (b).

14. A process for the production of lactic acid or a $C_{3-6}$ alkyl lactate comprising:
    a) reacting a stream rich in saccharide with sodium hydroxide in the presence of water to produce a reaction mixture comprising sodium lactate;
    (b) admixing at least a portion of the reaction mixture from step (a) with HCl and with a $C_{3-6}$ alkyl alcohol to produce a biphasic mixture comprising lactic acid and sodium chloride;
    (b') separating sodium chloride and water from lactic acid by liquid-liquid phase separation; and optionally
    (b'') reacting at least a portion of the lactic acid with the $C_{3-6}$ alkyl alcohol to produce $C_{3-6}$ alkyl lactate.

15. A process as claimed in claim 14, wherein the $C_{3-6}$ alkyl alcohol is n-butanol.

16. A process for the production of a $C_{1-6}$ alkyl lactate comprising:
    (a) reacting a stream rich in saccharide with sodium hydroxide in the presence of water to produce a reaction mixture comprising sodium lactate;
    (b) admixing at least a portion of the sodium lactate with HCl and with a $C_{1-6}$ alkyl alcohol to produce lactic acid and sodium chloride;
    (b'') reacting at least a portion of the lactic acid with the $C_{1-6}$ alkyl alcohol to produce the corresponding alkyl lactate; and
    (b''') separating sodium chloride and $C_{1-6}$ alkyl lactate.

17. A process as claimed in claim 16, wherein the $C_{1-6}$ alkyl alcohol is n-butanol.

18. A process as claimed in claim 8, wherein the alkyl lactate is recovered by distillation under reduced pressure.

19. A process as claimed in claim 1, additionally comprising converting the lactic acid into oligomeric lactic acid, lactide, alkyl lactyllactate, poly-lactic acid, propylene glycol, or acrylic acid.

20. A process as claimed in claim 8, additionally comprising converting the $C_{1-6}$ alkyl lactate into oligomeric lactic acid, lactide, alkyl lactyllactate, poly-lactic acid, propylene glycol, or acrylic acid.

\* \* \* \* \*